(12) United States Patent
Zeylikovich et al.

(10) Patent No.: US 7,006,676 B1
(45) Date of Patent: Feb. 28, 2006

(54) METHOD AND APPARATUS FOR DETECTING AN ABNORMALITY WITHIN A HOST MEDIUM UTILIZING FREQUENCY-SWEPT MODULATION DIFFUSION TOMOGRAPHY

(75) Inventors: Iosif Semen Zeylikovich, Charlotte, NC (US); Michael Victor Klibanov, Charlotte, NC (US); Andrey Anatolyevich Kharisov, Charlotte, NC (US)

(73) Assignee: Medical Optical Imaging, Inc., Charlotte, NC (US)

( * ) Notice: Subject to any disclaimer, the term of this patent is extended or adjusted under 35 U.S.C. 154(b) by 0 days.

(21) Appl. No.: 09/531,262

(22) Filed: Mar. 17, 2000

Related U.S. Application Data

(60) Provisional application No. 60/177,335, filed on Jan. 21, 2000.

(51) Int. Cl.
*G06K 9/00* (2006.01)
*A61B 1/06* (2006.01)
*H01S 3/10* (2006.01)

(52) U.S. Cl. .................. 382/131; 600/160; 372/28

(58) Field of Classification Search ............... 382/131, 382/128, 129, 130, 132, 133; 600/473, 476, 600/160, 180; 378/37; 356/320, 323; 372/28
See application file for complete search history.

(56) References Cited

U.S. PATENT DOCUMENTS 3,782,828 A    1/1974   Alfano et al.

(Continued)

FOREIGN PATENT DOCUMENTS

EP    0 826 958 A2    3/1998

(Continued)

OTHER PUBLICATIONS

*Global Uniqueness of a Class of Multidimensional Inverse Problems;* A.L. Buhgeim, et al.; Soviet Math. Dokl., vol. 24, No. 2, (1981).

(Continued)

*Primary Examiner*—Joseph Mancuso
*Assistant Examiner*—Shefali Patel
(74) *Attorney, Agent, or Firm*—Alston & Bird LLP

(57) ABSTRACT

Methods and apparatus are provided for detecting an abnormality in a host medium, such as a tumor within a patient's breast. The host medium is initially illuminated at a plurality of different positions with light of at least two different wavelengths. Following the propagation of the signals through the host medium, the amplitude and phase of the signals are detected and, based upon the detected signals, a shadow image can be created in which the abnormality is depicted as a suspicious region. Once a suspicious region has been identified, at least that portion of the host medium that contains the suspicious region is again illuminated with frequency-swept modulated signals of at least two different wavelengths generated by the light source and modulated by a modulator, such as a network analyzer. Based upon the detected signals that have propagated through at least that portion of the host medium that includes the suspicious region, a P-criteria can be determined that is dependent upon the coefficient of absorptivity of the host medium and embedded abnormalities. Likewise, an $S_{var}$-criteria can be determined based upon concentrations of oxygenated hemoglobin and deoxygenated hemoglobin. Based upon at least these criteria which reflect physiological parameters of the host medium and embedded abnormalities as well as the possible comparison of the shadow images to an x-ray image of the host medium, the abnormality can be characterized. In addition, an apparatus is provided that facilitates the compression of a patient's breast in order to improve the resulting images.

30 Claims, 8 Drawing Sheets

U.S. PATENT DOCUMENTS

| | | | |
|---|---|---|---|
| 3,811,777 A | | 5/1974 | Chance |
| 3,963,933 A | | 6/1976 | Henkes, Jr. |
| 3,973,126 A | | 8/1976 | Redington et al. |
| 4,075,883 A | | 2/1978 | Glover |
| 4,212,306 A | | 7/1980 | Mahmud |
| 4,515,165 A | | 5/1985 | Carroll |
| 4,653,855 A | * | 3/1987 | Birnbach et al. ........... 324/310 |
| 4,691,333 A | * | 9/1987 | Gabriele et al. .............. 378/37 |
| 4,850,002 A | | 7/1989 | Harding et al. |
| 4,945,239 A | | 7/1990 | Wist et al. |
| 4,972,331 A | | 11/1990 | Chance |
| 5,062,428 A | | 11/1991 | Chance |
| 5,070,455 A | | 12/1991 | Singer et al. |
| 5,079,697 A | | 1/1992 | Chesler |
| 5,079,698 A | | 1/1992 | Grenier et al. |
| 5,090,415 A | | 2/1992 | Yamashita et al. |
| 5,119,815 A | | 6/1992 | Chance |
| 5,122,974 A | | 6/1992 | Chance |
| 5,137,355 A | | 8/1992 | Barbour et al. |
| 5,187,672 A | | 2/1993 | Chance et al. |
| 5,213,105 A | | 5/1993 | Gratton et al. |
| 5,214,581 A | | 5/1993 | Rhodes et al. |
| 5,274,716 A | | 12/1993 | Mitsuoka et al. |
| 5,297,033 A | | 3/1994 | Bito et al. |
| 5,327,286 A | | 7/1994 | Sampsell et al. |
| 5,335,257 A | | 8/1994 | Sunberg |
| 5,349,954 A | | 9/1994 | Tiemann et al. |
| 5,353,799 A | | 10/1994 | Chance |
| 5,373,443 A | | 12/1994 | Lee et al. |
| 5,386,827 A | | 2/1995 | Chance et al. |
| 5,402,778 A | | 4/1995 | Chance |
| 5,413,098 A | | 5/1995 | Benaron |
| 5,416,582 A | | 5/1995 | Knutson et al. |
| 5,424,843 A | | 6/1995 | Tromberg et al. |
| 5,428,447 A | | 6/1995 | Toida |
| 5,539,797 A | | 7/1996 | Heidsieck et al. |
| 5,553,614 A | | 9/1996 | Chance |
| 5,555,885 A | | 9/1996 | Chance |
| 5,564,417 A | | 10/1996 | Chance |
| 5,590,166 A | * | 12/1996 | Suni et al. ..................... 378/37 |
| 5,592,085 A | | 1/1997 | Ehman |
| 5,596,987 A | | 1/1997 | Chance |
| 5,628,314 A | | 5/1997 | Kumagai |
| 5,664,574 A | | 9/1997 | Chance |
| 5,673,701 A | | 10/1997 | Chance |
| 5,692,511 A | | 12/1997 | Grable |
| 5,694,938 A | | 12/1997 | Feng et al. |
| 5,699,798 A | | 12/1997 | Hochman et al. |
| 5,704,355 A | | 1/1998 | Bridges |
| 5,713,352 A | * | 2/1998 | Essenpreis et al. ......... 600/407 |
| 5,713,364 A | | 2/1998 | DeBaryshe et al. |
| 5,719,399 A | | 2/1998 | Alfano et al. |
| 5,722,406 A | | 3/1998 | Papaioannou |
| 5,722,407 A | | 3/1998 | Klingenbeck-Regn et al. |
| 5,779,631 A | | 7/1998 | Chance |
| 5,782,755 A | | 7/1998 | Chance et al. |
| 5,799,656 A | * | 9/1998 | Alfano et al. ............... 600/473 |
| 5,807,257 A | | 9/1998 | Bridges |
| 5,807,262 A | | 9/1998 | Papaioannou et al. |
| 5,813,988 A | | 9/1998 | Alfano et al. |
| 5,840,035 A | | 11/1998 | Heusmann et al. |
| 5,853,370 A | | 12/1998 | Chance et al. |
| 5,873,821 A | | 2/1999 | Chance et al. |
| 5,876,339 A | | 3/1999 | Lemire |
| 5,877,856 A | | 3/1999 | Fercher |
| 5,899,865 A | | 5/1999 | Chance |
| 5,907,406 A | | 5/1999 | Papaioannou et al. |
| 5,917,190 A | | 6/1999 | Yodh et al. |
| 5,938,613 A | | 8/1999 | Shmulewitz |
| 5,941,827 A | | 8/1999 | Papaioannou |
| 5,943,133 A | | 8/1999 | Zeylikovich et al. |
| 5,952,664 A | | 9/1999 | Wake et al. |
| 5,954,053 A | | 9/1999 | Chance et al. |
| 5,963,658 A | | 10/1999 | Klibanov et al. |
| 5,983,121 A | * | 11/1999 | Tsuchiya ..................... 600/310 |
| 5,987,351 A | | 11/1999 | Chance |
| 5,999,836 A | | 12/1999 | Nelson et al. |
| 6,002,958 A | | 12/1999 | Godik |
| 6,023,341 A | | 2/2000 | Colak |
| 6,049,583 A | | 4/2000 | Galkin |
| 6,058,324 A | | 5/2000 | Chance |
| 6,061,589 A | * | 5/2000 | Bridges et al. ............. 600/430 |
| 6,064,917 A | | 5/2000 | Matson |
| 6,091,983 A | | 7/2000 | Alfano et al. |
| 6,480,565 B1 | * | 11/2002 | Ning ............................ 378/37 |
| 6,671,540 B1 | * | 12/2003 | Hochman .................... 600/431 |

FOREIGN PATENT DOCUMENTS

| | | |
|---|---|---|
| WO | WO 92/12705 A1 | 8/1992 |
| WO | WO 92/13598 A1 | 8/1992 |
| WO | WO 92/20273 A2 | 11/1992 |
| WO | WO 94/21173 A1 | 9/1994 |
| WO | WO 95/02987 A2 | 2/1995 |
| WO | WO 95/12132 A1 | 5/1995 |
| WO | WO 96/32632 A1 | 10/1996 |
| WO | WO 97/08538 A1 | 3/1997 |
| WO | WO 99/40840 | 8/1999 |
| WO | WO 99/40841 | 8/1999 |
| WO | WO 99/40842 | 8/1999 |

OTHER PUBLICATIONS

*On a Class of Inverse Problems;* M.V. Klibanov; Soviet Math. Dokl., vol. 26, No. 1, (1982).

*On the Solution of Coefficient Inverse Problems by the Method of Quasi-Inversion;* M.V. Klibanov, et al.; Soviet Math. Dokl., vol. 41, No. 1 (1990).

*Newton-Kantorovich Method for Three-Dimensional Potential Inverse Scattering Problem and Stability of the Hyperbolic Cauchy Problem with Time-Dependent Data;* Michael V. Klibanov, et al.; Inverse Problems 7, 577-596, (1991).

*Inverse Problems and Carleman Estimates;* Michael V. Klibanov; Inverse Problems 8, 575-596, (1992).

*Phaseless Inverse Scattering and the Phase Problem in Optics;* Michael V. Klibanov, J. Math. Phys. 33, (11), Nov., 1992.

*Numerical Solution of a Time-Like CauchyProblem for the Wave Equation;* Michael Klibanov; Mathematical Methods in the Applied Sciences, vol. 15, 559-570, (1992).

*Two Versions of Quasi-Newton Method for Multidimensional Inverse Scattering Problem;* Semion Gutman, et al.; Journal of Computational Acoutics, vol. 1, No. 2, 197-228, (1993).

*Regularized Quasi-Newton Method for Inverse Scattering Problems;* S. Gutman, et al.; Math. Comput. Modeling, vol. 18, No. 1, pp. 5-31, (1993).

*Mathematics and Physics of Emerging Biomedical Imaging;* Committee on the Mathematics and Physics of Emerging Dynamic Biomedical Imaging; SPIE Proceedings, vol. 2570, (1995).

*Global Convexity in a Single-Source 3-D Inverse Scattering Problem;* Semion Gutman, et al.; IMA Journal of Applied Mathematics, 55, 281-302, (1995).

*Mapping of Photon Distribution and Imaging of MR-Derived Anatomically Accurate Optical Models of the Female Breast;* San-Lian S. Barbour, et al.; Proceedings of SPIE, vol. 2389, (1995).

Analysis of Time-Resolved Data For Tomographical Image Reconstruction of Opaque Phantoms and Finite Absorbers in Diffusive Media; B.B. Das, et al.; SPIE, vol. 2384, (1995).
*Uniform Strict Convexity of a Cost Functional for Three-Dimensional Inverse Scattering Problem;* Michael V. Klibanov, et al.; SIAM J. Math, Anal., vol. 26, No. 1, pp. 147-179, Jan., 1995.
*Frequency-Domain Multichannel Optical Detector for Noninvasive Tissue Spectroscopy and Oximetry;* Sergio Fantini, et al.; Optical Engineering 34(1), 32-42, Jan., 1995.
*Detecting Technologies for Mines and Minelike Targets;* Abinash C. Dubey, et al.; SPIE Proceedings, vol. 2496, Apr., 1995.
*Ultrafast Photonic Materials and Applications;* Robert R. Alfano, et al.; New York State Center for Advanced Technology, The City University of New York, Dec., 1995.
*Frequency-Domain Optical Mammography: Edge Effect Corrections;* Sergio Fantini, et al.; Med. Phys. 23 (1), Jan. 1996.
*Characterization of Female Breasts in Vivo by Time Resolved and Specroscopic Measurements in Near Infrared Spectroscopy;* Hans Heusmann, et al.; Journal of Biomedical Optics 1(4), 425-434, Oct., 1996.
*Non-Invasive Measurements of Breast Tissue Optical Properties Using Frequency-Domain Photon Migration;* Bruce J. Tromberg, et al.; Phil. Trans. R. Soc. Land. B, 661-668, (1997).
*Detection and Characterization of Optical Inhomogeneities with Diffuse Photon Density Waves: A Signal-to-Noise Analysis;* D.A. Boas, et al.; Applied Optics, vol. 36, No. 1, Jan., 1997.

*Frequency-Domain Techniques Enhance Optical Mammography: Initial Clinical Result;* Maria Angela Franceschini, et al.; Proc. Natl Acad. Sci., USA, vol. 94, pp. 6468-6473, Jun., 1997.
PCT International Search Report Relating to International Application No. PCT/US98/01056; University of North Carolina, et al.; Entitled: *Method and Apparatus for Detecting an Abnormality Within a Scattering Medium;* Jan., 1998.
*Development of Time-Domain Optical Mammograph and First In Vivo Applications;* Dirk Grosenick, et al.; Applied Optics, vol. 38, No. 13, May, 1999.
*Globally Convergent Numerical Method in Diffusion Tomography;* Michael V. Klibanov; Department of Mathematics, University of North Carolina at Charlotte, SPIE Proceedings, vol. 2570, (1995).
*Mapping of Photon Distribution and Imaging of MR-Derived Anatomically Accurate Optical Models of the Female Breast;* San-Lian S. Barbour, et al.; SPIE vol. 2389, pp. 835-850, (1995).
*Consideration of Solutions to the Inverse Scattering Problem for Biomedical Applications;* Michael V. Klibanov, et al.; SPIE vol. 1887, pp. 77-96, (1993).
*Underwater Electro-Optical System For Mine Identifcation,* STRAND, SPIE Proceedings, vol. 2496, pp. 487-493, Apr., 1995.
*Underwater Detection Using Coherent Imaging Techniques,* Caimi, et al., SPIE Proceedings, vol. 2496, Apr., 1995.

\* cited by examiner

METHOD AND APPARATUS FOR DETECTING AN ABNORMALITY WITHIN A HOST MEDIUM UTILIZING FREQUENCY-SWEPT MODULATION DIFFUSION TOMOGRAPHY

RELATED APPLICATIONS

The present application claims priority from U.S. Provisional Application No. 60/177,335 filed Jan. 21, 2000, the contents of which are incorporated herein.

GOVERNMENT LICENSE RIGHTS

The U.S. Government may have rights in this invention as provided for by the terms of SBIR Grant No. DMS-9704923 awarded by the National Science Foundation.

FIELD OF THE INVENTION

The present invention relates generally to detection methods and apparatus and, more particularly, to methods and apparatus for detecting an abnormality within a host medium.

BACKGROUND OF THE INVENTION

Imaging systems are widely utilized to construct an image or model of a structure which is otherwise unobservable to the eye. Typically, imaging systems are designed to detect abnormalities, foreign objects or other structures which are embedded within a host medium and which alter or perturb the signal propagation properties of the host medium. For example, x-ray tomography and other medical imaging techniques are commonly used to create an image of a portion of the human body such that tumors or other inclusions can be detected. Similarly, imaging systems have been developed to detect deposits of oil or other minerals within the earth or to detect mines, such as mines buried underground or at sea.

By way of example, a variety of imaging systems have been developed to create an image of the human breast. These imaging systems are particularly important since breast cancer kills many women every year. For example, breast cancer is the leading cause of death for women ages 35 to 50 and the second leading cause of death for women over 50. The key to surviving breast cancer, however, is early detection and diagnosis. Currently, x-ray mammography is the most widely utilized technique for radiologically examining the human breast. Unfortunately, x-ray mammography exposes the patient to ionizing radiation which is a known cause of cancer. X-ray mammography also generally requires that the patient's breast be greatly compressed, such as to 4 centimeters, which can be quite painful. In addition, the images obtained by x-ray mammography techniques are not always of a sufficiently high quality to detect masses in the patient's breast, particularly for patients having radiodense breast tissue. The images produced by x-ray mammography techniques also do not clearly delineate between benign and malignant tumors. Thus, women who are found to have suspicious masses are generally required to undergo an invasive procedure, such as a biopsy, in which a portion of the mass is collected for analysis. At least in those instances in which the mass is found to be benign, the biopsy will generally have been unnecessary. As a result of the limitations of x-ray mammography techniques, a variety of other imaging techniques have been developed; particularly for the detection of breast cancer.

For example, magnetic resonance imaging, positron emission tomography, ultrasound imaging and thermography have been developed. Unfortunately, each of these imaging techniques suffers from a number of shortcomings. For example, while magnetic resonance imaging generally provides acceptable images, a magnetic resonance imaging machine is extremely expensive and is therefore not commonly utilized for breast cancer diagnosis.

Optical imaging techniques are now being developed as a potential alternative tomography technique. Since optical imaging utilizes non-ionizing radiation, the patient can be repeatedly or continuously exposed without harmful side effects. In addition, optical imaging techniques are non-invasive and are relatively economical relative to other imaging techniques, such as positron emission tomography or magnetic resonance imaging. Optical imaging techniques are also advantageous since the optical properties of the breast do not generally depend upon the patient's age and typically require only a gentle compression of the breast.

Similar to other known mammography techniques, optical imaging systems introduce light into a host medium, such as a patient's breast, and create an image of the host medium and abnormalities within the host medium based upon the interaction of the light with the host medium and the abnormalities. Due to differences between the optical properties of the host medium and the abnormalities, the abnormalities interact with the light in a different manner than the host medium. For example, the absorption coefficient and the scattering coefficient of an abnormality is typically substantially different than the absorption coefficient and the scattering coefficient of the host medium. Based upon the detected signals, an image of the host medium and abnormalities within the host medium can be created. Furthermore, optical characteristics of the host medium and, more importantly, abnormalities within the host medium can be determined. As such, optical imaging techniques offer the promise of permitting abnormalities to be characterized in a non-invasive manner. For example, optical imaging techniques may not only permit suspicious masses to be detected within a patient's breast, but may also permit benign and malignant tumors to be differentiated without requiring a biopsy or other invasive procedure.

Unfortunately, the strongly diffusive nature of light propagation in breast tissue significantly reduces the contrast and resolution of the optical images obtained by most optical imaging techniques. As such, optical imaging techniques have had difficulty consistently detecting and characterizing suspicious lesions, such as tumors, that are relatively small and/or deep within the breast.

With respect to these optical imaging techniques, a transillumination technique, also known as diaphanography or light scanning, was initially explored in which the patient's breast was illuminated with a continuous wave, broad beam light source. These transillumination techniques also employed a detector, such as a video camera, on the opposite side of the breast from the light source for detecting signals following propagation through the breast. Unfortunately, continuous wave transillumination techniques generally suffered from relatively low sensitivity and/or a relatively high number of false positive results.

As such, other optical imaging techniques have been developed that utilize laser light in order to provide images having increased resolution and sensitivity. These optical imaging techniques are practiced in both the time-domain and the frequency-domain. In the time-domain, the patient's breast is illuminated with a series of short pulses of light. By examining the manner in which the light pulses are altered during propagation through the patient's breast, an image of the patient's breast can be constructed. In the frequency-domain, however, the intensity of the light source is modulated at one or more frequencies, typically on the order of $10^8$ Hz. Based upon the signals detected following propagation through the patient's breast, the phase shift and amplitude attenuation of the signals can be determined and a corresponding image of the patient's breast can be constructed. See, for example, the elliptic systems methodology described by U.S. Pat. No. 5,963,658 to Klibanov, et al., the contents of which are incorporated herein by reference. While these other optical imaging techniques are quite promising, particularly in conjunction with the early detection and characterization of breast cancer, further improvements to these optical imaging systems are desired in order to further improve the contrast and resolution of the optical images and the reliability with which physiological parameters that define the abnormality can be determined in order to accurately characterize the nature of an abnormality.

SUMMARY OF THE INVENTION

The present invention therefore provides an improved method and apparatus for detecting an abnormality in a host medium, such as a mass, i.e., a tumor, within a patient's breast. According to the method and apparatus of the present invention, various physiological parameters defining the abnormality can be determined which permit the abnormality to be accurately characterized without requiring a biopsy or other invasive procedure. In addition, the method and apparatus of the present invention can create an image of the host medium with sufficient contrast and resolution to permit abnormalities such as tumors, to be detected at an early stage in order to increase the patient's chances of survival.

According to one embodiment, the host medium is initially illuminated, typically by a light source, at a plurality of different positions. In this regard, the host medium is preferably illuminated at a plurality of different positions with signals having at least two different wavelengths of light. In addition, the method and apparatus of the present invention can include a modulator, such as a network-analyzer, for modulating the amplitude of the illuminating signals at a frequency selected from a predetermined range of frequencies. As such, the signals that illuminate the host medium at adjacent positions are typically modulated at different frequencies within the range of frequencies.

The method and apparatus of the present invention also includes a detector, such as a photomultiplier tube, for detecting signals following propagation through the host medium and abnormalities within the host medium. In this regard, at least an amplitude of signals and, more typically, an amplitude and a phase of the signals are detected following propagation through the host medium and abnormalities within the host medium. Based upon the detected signals, a shadow image can be created and presented upon a display in which the abnormality is depicted as a suspicious region. Since an abnormality, such as a malignant tumor, will typically attenuate the signals to a greater degree than the host medium, an abnormality is typically represented by a suspicious region of greater attenuation than the surrounding tissue. In embodiments in which the host medium is illuminated with signals having at least two different wavelengths, the method and apparatus of the present invention can form the ratio of the amplitude of the signals detected at at least one position at each of the different wavelengths and can display an image of this ratio in order to further highlight the suspicious region.

Once a suspicious region has been identified, at least that portion of the host medium that contains the suspicious region is again illuminated with frequency-swept modulated signals generated by the light source and modulated by a modulator, such as a network analyzer. In this regard, frequency-swept modulation refers to the modulation of the amplitude of the illuminating signals at a plurality of frequencies that sweep through a predetermined range of frequencies. For sake of reference, the range of frequencies through which the signals are frequency-swept modulated is larger, generally much larger, than the range of frequencies from which the modulation frequency of the signal that initially illuminates the host medium during the creation of the shadow image is selected. As before, the illumination of at least that portion of the host medium that contains the suspicious region is conducted at each of at least two different wavelengths. At each wavelength, the detector detects the signals that have propagated through at least that portion of the host medium that contains the suspicious region. Based upon the detected signals that have propagated through at least that portion of the host medium that includes the suspicious region, a P-criteria can be determined at at least one of a plurality of positions within the host medium that is dependent upon the coefficients of absorptivity of the host medium to signals having the different wavelengths. Likewise, an $S_{var}$-criteria can be determined at at least one of a plurality of positions within at least that portion of the host medium that contains the suspicious region based upon a variation in the percent concentration of oxygenated hemoglobin between the abnormality and the host medium and a variation in the total hemoglobin concentration between the abnormality and the host medium at the respective positions. Based upon at least these criteria which reflect physiological parameters of the host medium and abnormalities within the host medium, the abnormality can be characterized.

The apparatus of this embodiment of the present invention also includes a positioner for positioning the light source and the detector relative to the host medium. In this regard, the positioner initially positions the light source at a plurality of different positions that cover a broad portion of the host medium to facilitate generation of a shadow image. In particular, the positioner preferably maintains the light source and the detector in alignment by initially positioning the light source and detector at a plurality of different positions that cover a broad portion of the host medium to facilitate generation of the shadow image. Thereafter, the positioner positions the light source proximate that portion of the host medium that includes the suspicious region to facilitate characterization of the abnormality. In one step of this more focused illumination of at least that portion of the host medium that contains the suspicious region, the positioner positions the light source at a fixed position offset from the suspicious region and the positioner then moves the detector through a plurality of positions including at least one position that is aligned with the suspicious region. In another step, the light source and the detector are positioned in an offset relation on opposite sides of the host medium and the positioner then moves both the light source and the detector in tandem such that the offset relation is maintained. Based upon the signals detected following scanning of the host medium with the light source and the detector in both an aligned relationship and an offset relation, the location of the abnormality within the host medium can be determined.

The apparatus of this embodiment of the present invention can also include means for protecting the detector. In this regard, the apparatus can include a diaphragm for selectively controlling the intensity of light that is presented to the detector. In addition, the apparatus can include a reference light source for also illuminating the host medium with reference signals and a reference detector for detecting the reference signals following propagation through the host medium and abnormalities within the host medium. According to this embodiment, the apparatus can further include a shutter for preventing further detection of signals by the detector if the reference detector detects that the intensity of the reference signals exceeds a predetermined threshold.

In addition to the physiological parameters, such as the P-criteria and the $S_{var}$-criteria, that are determined by the apparatus and method of the present invention as well as the shadow image that is created at each wavelength, the method of the present invention can also characterize the abnormality based upon a comparison of the shadow image to an x-ray image and, more particularly, based upon a comparison of the suspicious region depicted by the shadow image to an x-ray image of the abnormality. In this regard, the shadow image can be overlaid onto the x-ray image and the abnormality can be characterized as possibly being a malignant tumor if the region of increased attenuation depicted as a suspicious region by the shadow image is substantially larger than the x-ray image of the abnormality. As such, the comparison of the shadow image to an x-ray image can serve to buttress the characterization of the abnormality based upon the physiological parameters, such as the P-criteria and the $S_{var}$-criteria, determined according to the method and apparatus of the present invention.

According to one aspect of the present invention that is particularly directed to the detection of masses, such as tumors, within a patient's breast, an apparatus for compressing the patient's breast in order to obtain improved images thereof is provided. According to this aspect of the present invention, the apparatus includes a pair of plates, typically transparent plates, separated by a distance sufficient to receive the patient's breast.

In order to move the pair of plates in order to appropriately compress the patient's breast, the apparatus of the present invention also includes means for moving the plates relative to one another. In addition, the apparatus can include a separation detector for measuring the distance by which the pair of plates are separated. The apparatus of this embodiment also includes an adjustable belt extending between the plates proximate the breast. The adjustable belt is capable of being tightened about the breast such that the breast fills a region defined by the pair of plates and the adjustable belt, thereby facilitating imaging of the breast.

Preferably, the apparatus of this embodiment also includes an opaque material that fills a region defined by the plates that is unfilled by the breast. In this regard, the adjustable belt can be operably connected to the opaque material, such as by extending through the opaque material, such that the opaque material is drawn about the breast as the adjustable belt is tightened. In order to identify any regions of separation between the opaque material and the breast, the apparatus of this embodiment can also include a background light to specifically illuminate the regions of separation. By tightening the belt about the breast such that the breast substantially fills the region defined by the pair of plates and the adjustable belt and also covering those portions of the plate that are unfilled by the breast with an opaque material, the apparatus and method of this embodiment of the present invention can obtain an improved image of the breast by substantially eliminating deleterious edge effects.

Accordingly, the method and apparatus of the present invention permits abnormalities to be detected within a host medium in a reliable and cost effective manner. In addition, the method and apparatus of the present invention permits physiological parameters that at least partially define the abnormality to be determined in order to characterize the abnormality. As such, the method and apparatus of the present invention can be advantageously utilized to provide early detection of suspicious lesions within a patient's breast and to appropriately characterize the suspicious lesions, such as being either malignant or benign, based upon physiological parameters that are determined from the detected signals without requiring a biopsy or other invasive procedure. By facilitating early detection and characterization of suspicious lesions within the patient's breast, the patient's chances of survival are substantially increased.

BRIEF DESCRIPTION OF THE DRAWINGS

FIGS. 3a and 3b are shadow images of a patient's breast for light signals having a wavelength of 680 nanometers and 830 nanometers, respectively, while

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

A method and apparatus for detecting an abnormality in a host medium will now be described in conjunction with the present invention. The method and apparatus of the present invention will be primarily described in conjunction with the detection of a tumor and, more particularly, the detection of a tumor or other mass in a patient's breast. However, the method and apparatus of the present invention can also be employed to detect abnormalities in a number of other host mediums, if so desired.

Figure 1:
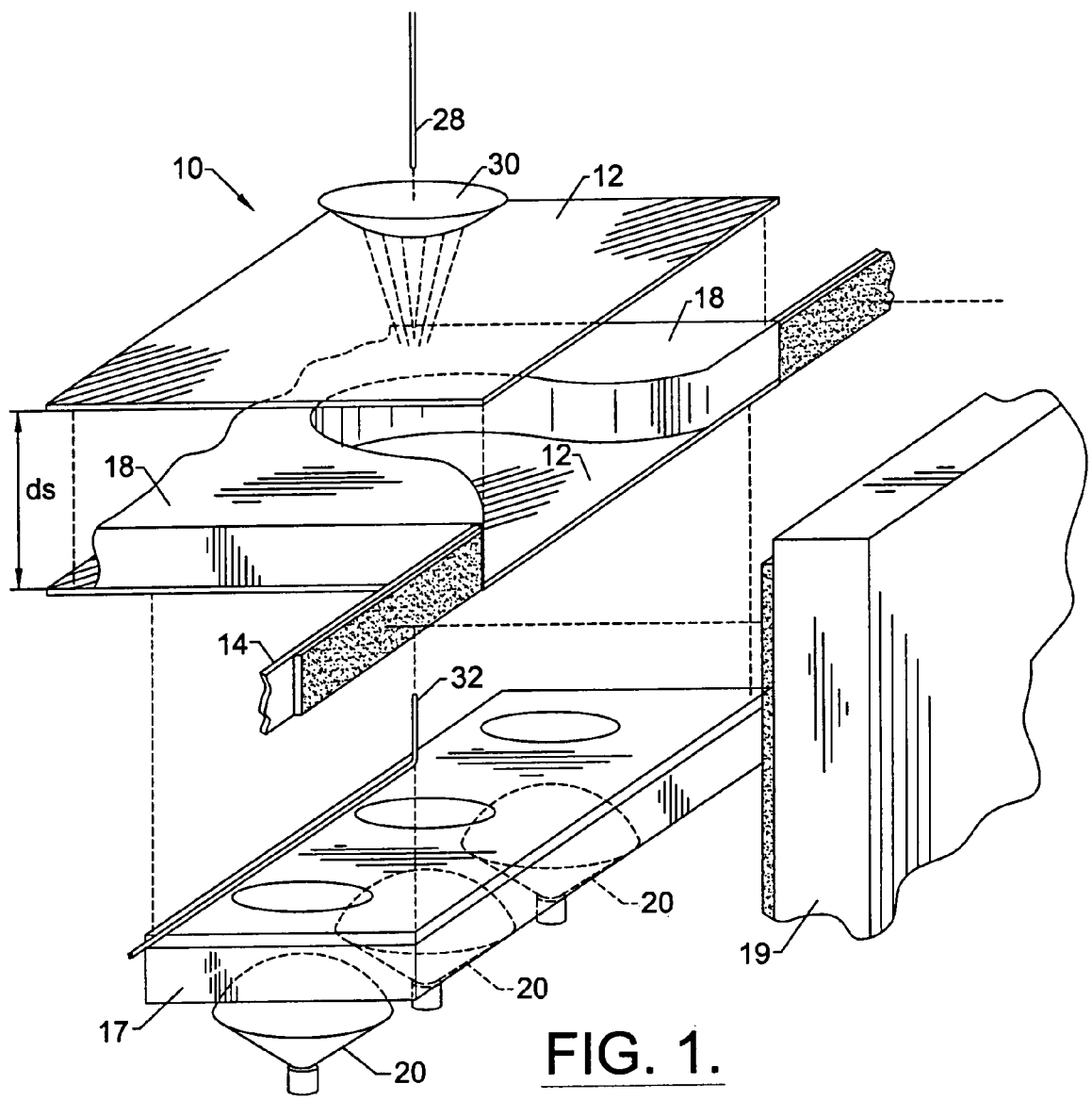
FIG. 1 is a perspective view of an apparatus for compressing a patient's breast according to one advantageous aspect of the present invention.

The detection method and apparatus of the present invention is essentially a two-step process in which a shadow image is initially created and then suspicious regions identified from the shadow image are further imaged in such a manner that physiological parameters relating to the abnormality can be determined and the abnormality can correspondingly be characterized. The creation of a reliable shadow image and the accuracy of the physiological parameters that are derived from further imaging of the suspicious regions are both dependent upon obtaining a true image of the patient's breast. As such, one aspect of the present invention involves properly positioning the patient's breast such that accurate images are obtained thereof. In this regard, an apparatus 10 for compressing a patient's breast according to one aspect of the present invention is depicted in FIG. 1.

As shown, the apparatus 10 includes a pair of plates 12 separated by a distance $d_s$, sufficient to receive the patient's breast. The plates are formed of a material that is substantially transparent to light of the wavelengths with which the patient's breast will subsequently be illuminated, as described below. Moreover, the plates are typically formed of a material that is also transparent to visible light such that the positioning and compressing of the patient's breast can be visually monitored by a physician, a technician, a nurse or the like. In one example, the plates are formed of an acrylic material.

The plates 12 are initially separated by a relatively large separation distance $d_s$, such that the patient's breast can be readily placed between the plates. Thereafter, at least one of the plates is advanced toward the other plate such that the patient's breast is compressed therebetween. Thus, the apparatus 10 of this aspect of the present invention includes means for positioning at least one of the plates. Although the plates can be positioned by a stepper motor or the like, the plates are frequently positioned manually. In order to improve the resulting image captured by the detection method and apparatus of the present invention, the patient's breast is preferably substantially compressed between the plates with the compression generally limited by the patient's discomfort level. The apparatus for compressing a patient's breast can also include a separation detector for measuring the separation between the plates following compression of the patient's breast therebetween. Once compression is complete, the separation detector provides a central controller or computer 40 that controls the overall operations of the detection method and apparatus with the separation distance for storage and use insubsequent curve fitting procedures.

Prior to placing the patient's breast between the pair of plates 12, the patient's breast is preferably covered with an oil having an index of refraction that substantially matches the index of refraction of the breast skin and/or other breast tissue in order to improve the resulting image. In one embodiment, for example, the patient's breast is covered with a light mineral oil, such as dermatoscopic oil 910 H/2. In addition to having an index of refraction that approximates the index of refraction of the breast skin, the oil is also preferably selected such that the oil is at least partially absorbed through the breast skin and into the blood stream so as to serve as a contrast agent. In one embodiment, therefore, a light mineral oil, such as dermatoscopic oil 910 H/2, is applied to the patient's breast and the patient then waits a predetermined period of time, such as ten minutes, until at least a portion of the oil has been absorbed into the blood stream to serve as a contrast agent prior to continuing with the imaging procedure. In addition to the oil or instead of selecting an oil that is capable of being absorbed into the blood stream, a contrast agent can be interveniously injected to increase the contrast during imaging operations. For example, a contrast agent of acetic acid can be interveniously injected.

In addition to improving the imaging process by approximating the index of refraction of the breast skin and serving as a contrast agent, the oil that is applied to the patient's breast has also been found to advantageously improve the amount by which the patient's breast can be compressed between the plates 12 without discomfort. By way of example, a typical patient's breast can be compressed to a thickness of about 6 centimeters in the absence of oil. Once oil has been applied to the same patient's breast, however, the breast can advantageously be compressed to about 5 centimeters, thereby significantly improving the quality of the images obtained by the detection method and apparatus of the present invention. Additionally, the application of oil to a patient's breast prior to other imaging techniques, such as an x-ray mammogram, may also prove to similarly increase the amount that the patient's breast can be compressed without discomfort.

As shown in FIG. 1, the compression apparatus 10 of this embodiment also includes an adjustable belt 14, typically formed of a rubber material, that extends between the pair of plates 12 proximate the patient's breast. Advantageously, the width of the adjustable belt approximately equals the separation distance $d_s$ between the plates following compression of the patient's breast. The length of the belt that extends between the plates is capable of being adjusted and held in a fixed position, such as by means of the VELCRO™ attachment of the opposite ends of the belt to a fixed partition 19 or the like that is shown somewhat removed from the compression apparatus in FIG. 1 for the sake of clarity. As such, the adjustable belt may be tightened about the patient's breast in order to compress the patient's breast such that the patient's breast fills a region defined by the pair of plates and the adjustable belt and any air gaps between the plate and the patient's breast are eliminated, thereby substantially diminishing deleterious edge effects in order to facilitate the imaging process.

In order to further improve the imaging process, the compression apparatus 10 can also include an opaque material 18 that fills the region defined by the plates 12 that is unfilled by the patient's breast following tightening of the belt 14. The opaque material can be formed of a variety of materials. However, the opaque material of one embodiment is a blood plastic. While the opaque material can be positioned between the plates in a variety of manners, the compression apparatus of one advantageous embodiment has the adjustable belt operably connected to the opaque material such that tightening of the belt about the patient's breast draws the opaque material toward the patient's breast. In the illustrated embodiment, for example, the adjustable belt extends through the opaque material such that the adjustable belt draws the opaque material into contact with the patient's breast as the adjustable belt is tightened thereabout.

The opaque material 18 further diminishes deleterious edge effects and provides sharp contrast along the edge of the patient's breast. In order to visually inspect for gaps between the opaque material and the patient's breast prior to commencing imaging operations, the compression apparatus 10 of the present invention can also include one or more background lights 20 for illuminating at least that region along the edge of the patient's breast. If the physician, technician, nurse or the like detects the background light shining through a gap between the opaque material and the patient's breast, the opaque material can be further drawn toward the patient's breast in order to eliminate the gap and improve the resulting image. Once the opaque material is properly positioned, however, the background lights are extinguished. In the illustrated embodiment, the background lights are schematically depicted to be recessed within a stage 17 that is disposed beneath the plates 12.

Figure 2:
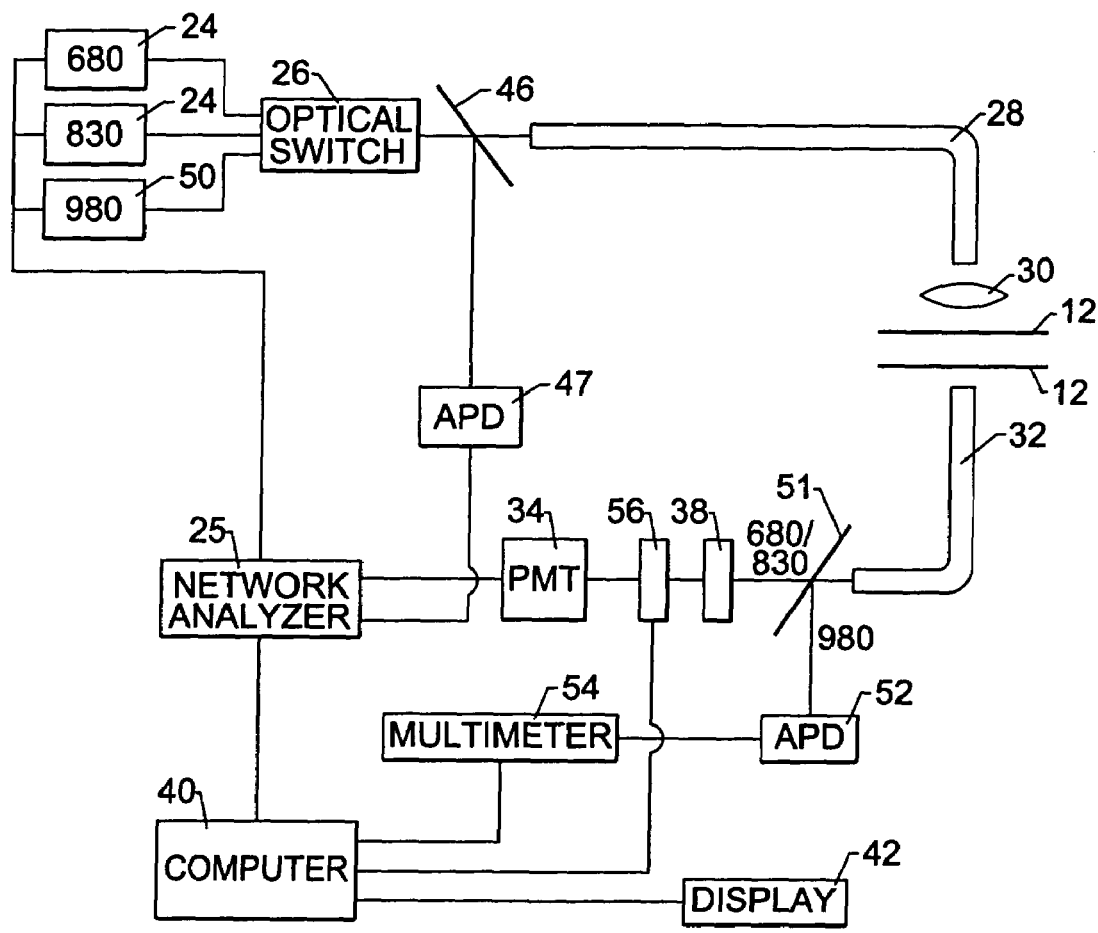
FIG. 2 is a block diagram of a detection method and apparatus according to another advantageous aspect of the present invention.

Once the patient's breast is appropriately positioned and compressed, a shadow image of the patient's breast is created. In this regard, FIG. 2 depicts a block diagram of one embodiment of the detection apparatus of the present invention. In order to create the shadow image, the host medium, i.e., the patient's breast, is illuminated at a plurality of different positions. Concurrent with the illumination, the signals that propagate through the patient's breast and abnormalities within the patient's breast are detected at at least one and, more preferably, each of the plurality of different positions. Based upon the detected signals, the shadow image is created in which the abnormality is depicted as a suspicious region.

In order to illuminate the patient's breast, the detection apparatus includes at least one and, more preferably, a pair of light sources 24, such as fiber optic pigtail diode lasers. Each diode laser emits light signals of a different wavelength, typically an infrared wavelength. For example, one light source may emit between 670 nanometers and 700 nanometers and, most preferably, about 680 nanometers, while the other light source may emit between 810 nanometers and 840 nanometers and, most preferably, about 830 nanometers. In this regard, the detection apparatus can include a thermoelectric cooler (TEC) for maintaining the diode lasers at a constant temperature to prevent temperature-induced wavelength fluctuations. In addition, while the diode laser can be driven to emit light signals having different power levels, the diode lasers typically emit light signals having a power level of between 100 and 500 milliwatts.

While the shadow image can be created by a variety of techniques including time-domain techniques, the detection method and apparatus of the present invention preferably utilizes the frequency-domain technique in which the amplitude of the light signals is modulated at a modulation frequency. The detection apparatus therefore preferably includes a modulator 25 for modulating the light signals such that the amplitude of the light signals is modulated at a frequency selected from a predefined range of frequencies. For example, the modulator can be a frequency-swept multichannel network analyzer, such as a Hewlett-Packard 8753E Network Analyzer that employs option 11, although other types of network analyzers as well as other types of modulators can be utilized.

As described below, the detection method and apparatus of the present invention illuminates the patient's breast at a plurality of different positions. For example, the patient's breast can be illuminated by a raster scanning technique in which the patient's breast is illuminated at a number of different positions arranged in a plurality of rows with each row having predetermined number of different positions. Although the shadow images can be created by modulating the amplitude of the light signal at a single modulation frequency, the detection method and apparatus of the present invention preferably utilizes a frequency sweeper, such as a frequency-swept network analyzer 25. As such, the amplitude of the light signals is preferably modulated at a plurality of different modulation frequencies selected from a predetermined range of frequencies. In one embodiment, for example, the amplitude of the light signals that illuminate the patient's breast at each position in a row is modulated at a different frequency. In one specific example in which the range of modulation frequency is 40 MHz to 40 MHz+10 kHz and in which each row includes a hundred different positions designated n=1 . . . 100, the amplitude of the light signal that illuminates each position is preferably modulated at a frequency of 40 MHz+(n(10 kHz))/100. This frequency modulation technique can then be repeated for each row until the entire breast has been scanned. It should be apparent, however, that the foregoing discussion is merely an example of one technique by which the amplitude of light signals can be frequency modulated at a plurality of frequencies selected from a predetermined range of frequencies and the amplitude of the light signals can be frequency modulated in a wide variety of other manners without departing from the spirit and scope of the present invention.

The frequency modulated light signals are directed to an optical switch 26. The optical switch selects one of the frequency modulated laser signals to illuminate the patient's breast. For example, the patient's breast is typically illuminated at a plurality of different positions with light signals of a first wavelength, such as 680 nanometers, prior to being illuminated at each of the plurality of positions by light of the second wavelength, such as 830 nanometers. The light signals selected by the optical switch are delivered to the patient's breast by means of an optical fiber 28. Although various types of optical fibers can be utilized, an optical fiber having a diameter of 100 micrometers can be employed. In addition, while the optical fiber can deliver the selected light signals directly to the patient's breast, the detection method and apparatus can include one or more focusing lens 30 disposed between the end of the optical fiber and the patient's breast in order to appropriately focus and direct the light signals.

In order to protect the patient from undesirably high power levels, the detection method and apparatus preferably includes means for measuring the power of the light signals delivered to the patient, such as by means of a handheld power meter. If the reading of the power meter exceeds a predetermined maximum power level, the detection method and apparatus can be adjusted such that the light signals have less power prior to exposing the patient to undesirably high power levels.

As shown in FIG. 1, the end of the optical fiber 28 as well as any focusing lenses 30 can be disposed on one side of the patient's breast, while another optical fiber 32 that is disposed in optical communication with a detector 34 described below is positioned on the opposite side of the patient's breast. As described above in connection with the optical fiber that delivers the light signals, the optical fiber that receives the signals following propagation through the patient's breast and delivers the light signals to the detector can, but need not necessarily, also include one or more focusing lenses (not shown) disposed between the end of the optical fiber and the patient's breast for directing the light signals to the optical fiber. In addition, while various different types of optical fibers can be utilized, the optical fiber of one advantageous embodiment has a diameter of 5 to 6 millimeters.

In creating the shadow image, the optical fibers 28, 32 that deliver and receive the light signals are preferably positioned in alignment, albeit on opposite sides of the patient's breast. The optical fibers are then moved in unison to each of the plurality of positions across the patient's breast such that light signals can be delivered to the patient's breast at each of the positions and light signals can be received following propagation through the patient's breast at each of the positions. Although the positions at which light is introduced into the patient's breast can be determined in a variety of manners, the detection method and apparatus of one embodiment of the present invention moves the optical fibers that deliver and receive light signals in tandem in a raster scanning motion to cover most, if not all, of the patient's breast. In order to appropriately move the optical fibers that deliver and receive the light signals, the detection apparatus preferably includes at least two X-Y linear motorized stages associated with each of the optical fibers that are capable of moving each optical fiber in a direction toward and away from the patient and in a direction from side to side relative to the patient. As such, the optical fibers that deliver and receive the light signals can be raster scanned across the majority of the patient's breast.

The detection apparatus of the present invention also preferably includes a detector 34 disposed in optical communication with the optical fiber 32 that receives the light signals following propagation through the patient's breast. Although the detection apparatus can include various types of detectors, the detector of one advantageous embodiment is a photomultiplier tube (PMT), such as a Hamamatsu R928 PMT, that is supplied power, such as 1100 volts, by a power source. Since a photomultiplier tube has a relatively small dynamic range, the power level of signals delivered to the detector is initially sampled to insure that the signals can be reliably detected by the photomultiplier tube. In this regard, a center portion of the patient's breast is typically illuminated and the power level of the signals received following propagation through the patient's breast is measured by the photomultiplier tube.

If the power level of the signals delivered by the optical fiber 32 to the photomultiplier tube 34 is excessive, the power level of the signals can be adjusted by controlling the intensity of the light that is delivered to the photomultiplier tube. For example, the detection apparatus can include a diaphragm 38 disposed between the optical fiber and the photomultiplier tube for selectively controlling the intensity of light that is delivered to the photomultiplier tube. Alternatively, the optical fiber can be moved, typically in a lateral direction, relative to the input port of the photomultiplier tube such that a desired intensity of light is delivered to the photomultiplier tube.

The output electrical signal of the photomultiplier tube 34 and, in particular, the amplitude and phase of the output electrical signal are dependent not only upon the light signals detected by the photomultiplier tube, but also the frequency response of the photomultiplier tube. In other words, the amplitude and phase response of a photomultiplier tube typically varies with frequency. Thus, the photomultiplier tube is preferably initially calibrated over a wide range of frequencies before detecting signals that have propagated through a patient. The resulting output signals provided by the photomultiplier tube during the analysis of a patient's breast can then be adjusted to compensate for the amplitude and phase response to the photomultiplier tube at different modulation frequencies. In this regard, for a photomultiplier tube having an amplitude and phase response of $A_0$ and $\phi_0$ at the frequency of interest, the true amplitude A of a detected signal can be defined as $A = A_{pmt}/A_0$ and the true phase can be defined as $\phi = \phi_{pmt} - \phi_0$ in which $A_{pmt}$ and $\phi_{pmt}$ are the amplitude and phase of the output signals provided by the photomultiplier tube prior to calibration. As such, the central controller or computer 40 can be configured to compensate for the amplitude and phase response of the photomultiplier tube at different frequencies of interest, such as the frequency variations introduced by frequency-swept modulation described below.

Figure 3A:
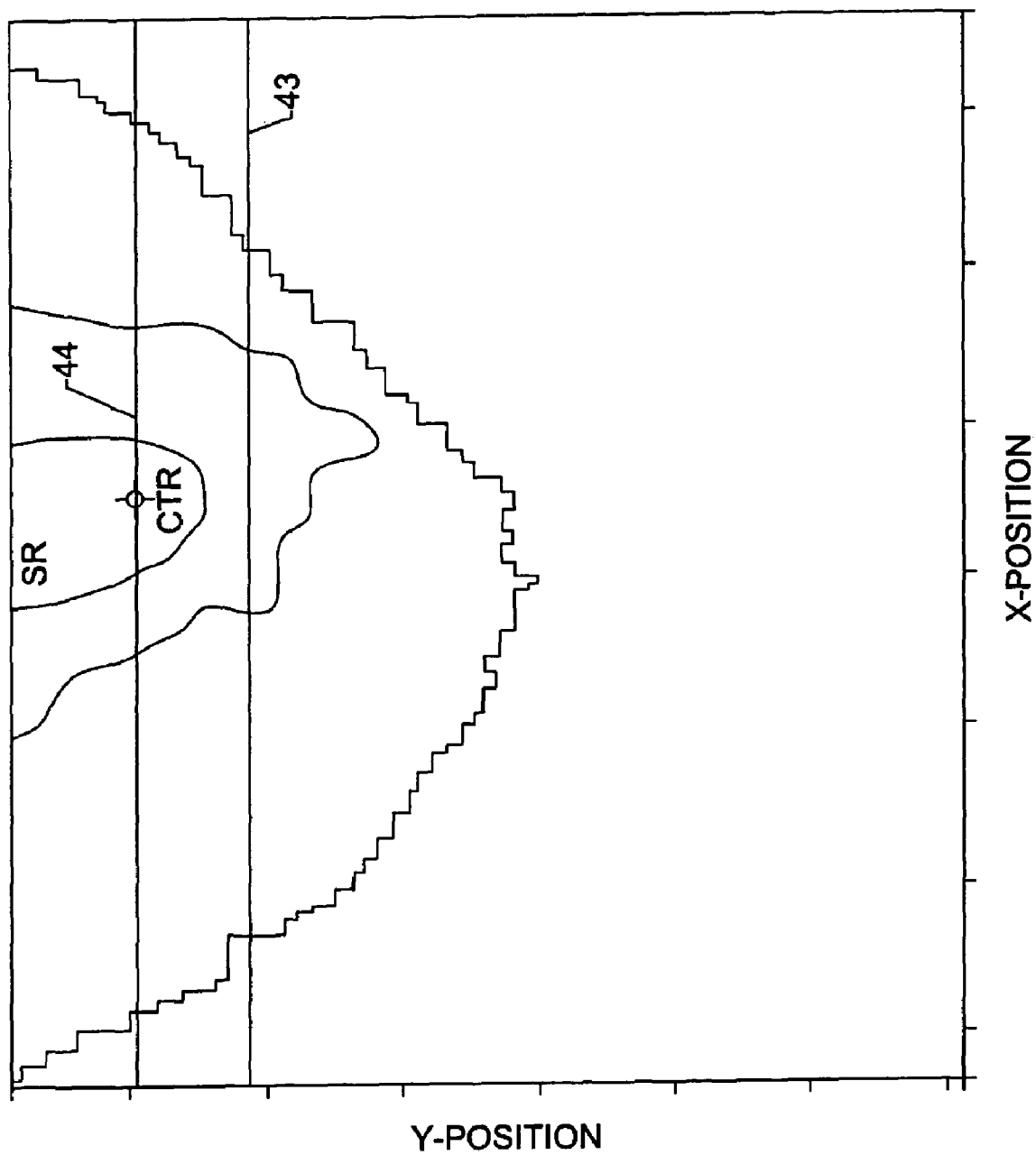
Figure 3B:
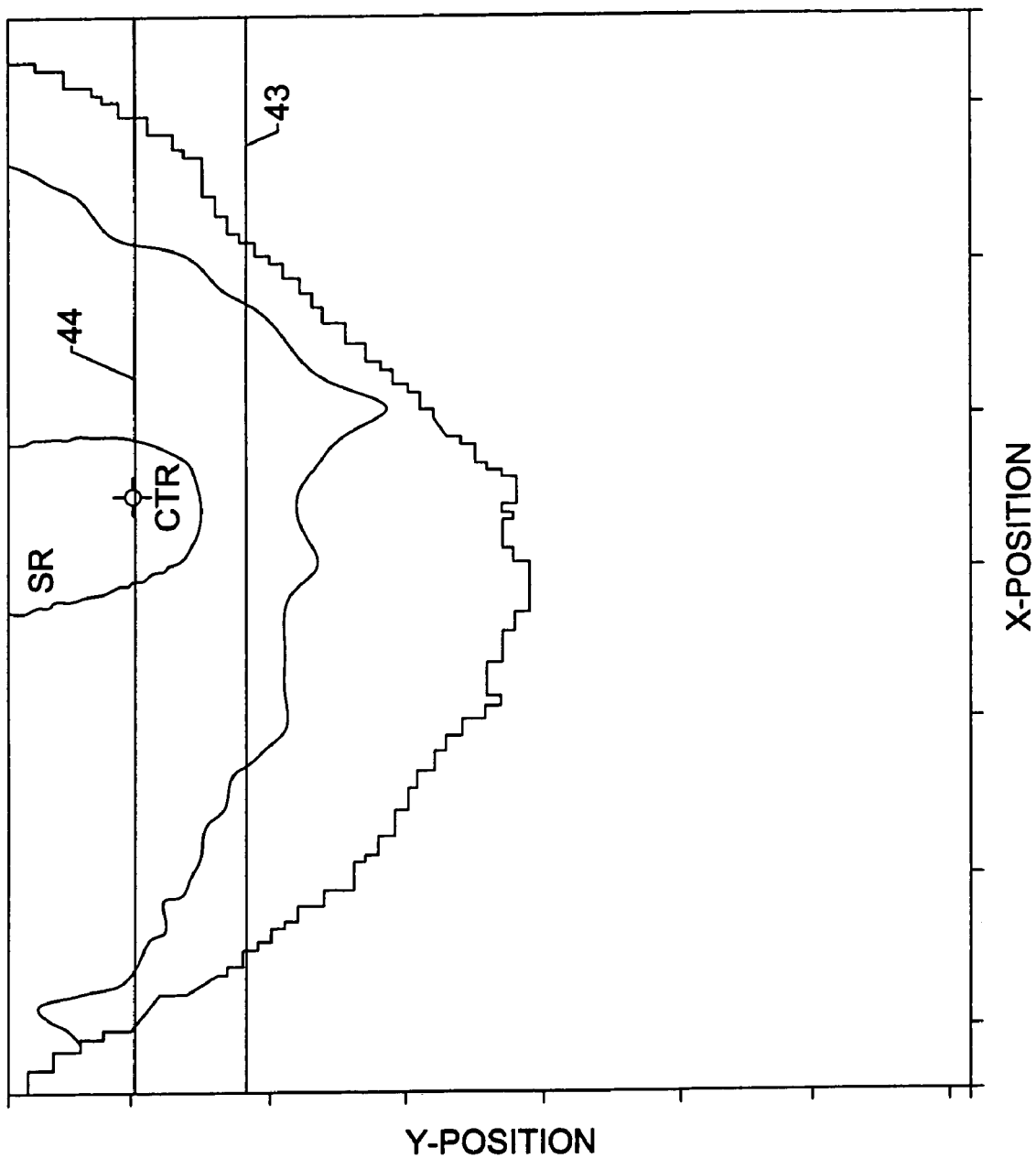

The signals detected by the photomultiplier tube 34 are provided to the network analyzer 25 and, in turn, to the central controller or computer 40 through a parallel interface, such as a GPIB interface, and a shadow image of the patient's breast is created, typically by means of Lab-VIEW™ software (provided by National Instruments Corp. of Austin, Tex.) operating on the central computer. In this regard, although the network analyzer determines the amplitude and phase shift of the light signals at each of the plurality of locations at which the patient's breast is illuminated, the resulting shadow image is typically based only upon the amplitude. The resulting shadow image can then be presented upon an associated display 42. In instances in which the patient's breast is illuminated with light signals having at least two different wavelengths, a shadow image of the patient's breast is typically created at each wavelength. See, for example, FIGS. 3a and 3b for examples of a shadow image created from light signals having wavelengths of 680 nanometers and 830 nanometers, respectively. While benign masses may absorb either more or less light than healthy breast tissue, malignant tumors have been found to consistently attenuate light to a greater degree than healthy breast tissue. As such, areas of the resulting shadow images that represent light signals that have been substantially attenuated are typically considered suspicious regions that merit further analysis. See, for example, the region designated SR in FIGS. 3a and 3b.

Figure 3C:
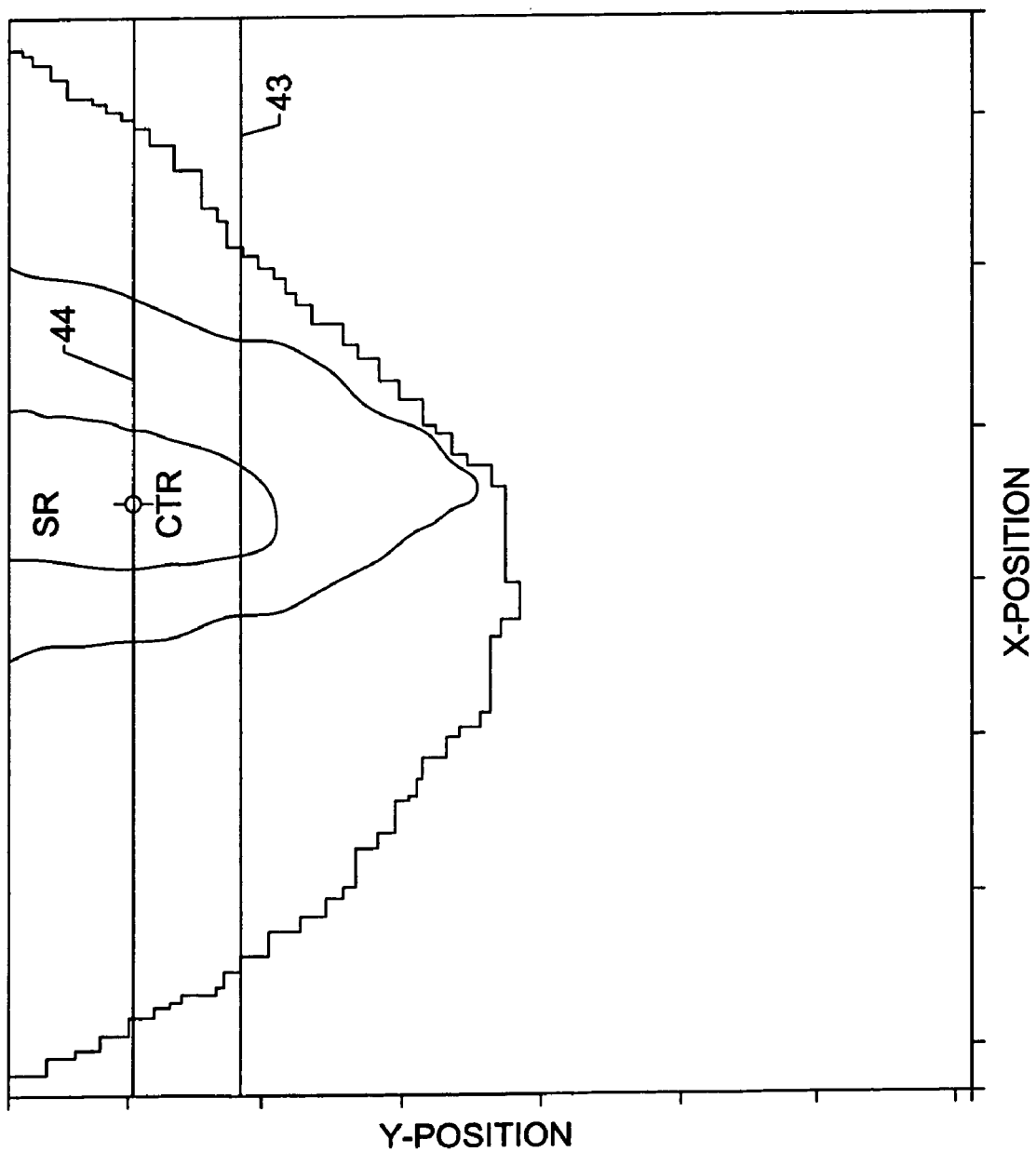
FIG. 3c is an image of the ratio of the shadow image of FIG. 3a to the shadow image of FIG. 3b.

The absorption coefficient $\mu_a$ of breast tissue is dependent upon the wavelength of light at which the breast tissue is illuminated. For normal breast tissue, the absorption coefficient for light having a wavelength of 680 nanometers is less than the absorption coefficient for light having a wavelength of 830 nanometers. Although not wishing to be bound by theory, it is believed that the inverse is true for a majority of malignant tumors in that the absorption coefficient of malignant tumors is greater for light having a wavelength of 680 nanometers than for light having a wavelength of 830 nanometers. As such, the ratio of the intensity of the detected light at at least one and, more preferably, each of the plurality of positions for light having wavelengths of 680 nanometers and 830 nanometers can be formed in order to further accentuate suspicious regions in which a substantially greater percentage of the incident light, particularly the incident light having a wavelength of 680 nanometers, was absorbed. See FIG. 3c for a shadow image of the ratio of the intensity of the detected light at 680 nanometers to the intensity of detected light at 830 nanometers.

In order to improve the reliability and consistency of the light signals detected by the photomultiplier tube 34 that are provided to the network analyzer 25 and, in turn, to the central controller or computer 40, the network analyzer and/or the central controller or computer can be configured to dynamically compensate for fluctuations in the power level of the light signals delivered to the patient, typically as a result of variations in the power that drives the light sources 24. In this regard, the detection method and apparatus can include a splitter 46, such as a fiber optic splitter, positioned between the optical switch and the patient in order to divert a predetermined percentage of the light signals, such as 0.5%. The splitter directs the diverted light signals to an avalanche photodiode 47 that, in turn, provides a signal representative of the power level of the light signals to the network analyzer which is designed to automatically compensate the light signals that are provided to the network analyzer following propagation through the patient's breast for power fluctuations that are evident from the diverted light signals.

Figure 4:
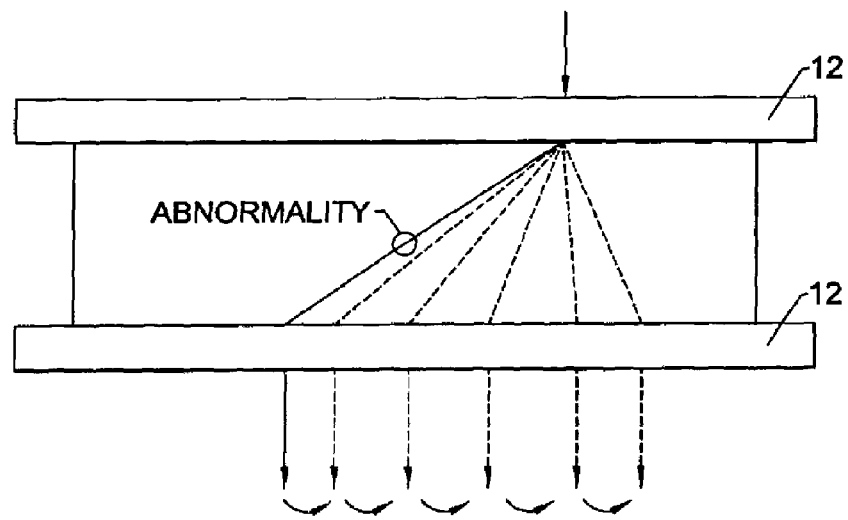
FIG. 4 is a schematic side elevational view of the more focused illumination of a region about a suspicious region in which the optical fiber that delivers the light signals is fixed at a position offset from the suspicious region.

Once one or more suspicious regions have been identified in a shadow image, the detection method and apparatus of the present invention contemplates further investigation of the suspicious regions. First, the reference absorption coefficient and the reference scattering coefficient are determined. In particular, the reference absorption coefficient and the reference scattering coefficient are determined by positioning the optical fibers that deliver and receive the light signals at one or more locations that are clearly displaced from the suspicious region such that the absorption and scattering coefficients that are determined from the amplitude and phase of the detected signals are representative of the host medium, i.e., healthy breast tissue, and can therefore also serve as reference values. In this regard, the optical fiber 28 that delivers the light signals is positioned at a fixed position offset from the suspicious region SR. See FIG. 4. While the optical fiber that delivers the light signals can be positioned at various distances from the suspicious region depending upon the size of the suspicious region and other factors, the optical fiber that delivers the light signals is typically positioned between about 8 and 20 mm and, more typically, about 14 mm from the center of the suspicious region. While the optical fiber that delivers light signals can be positioned in any direction relative to the suspicious region, the optical fiber that delivers the light signals is preferably positioned closer to the center of the patient's breast than an edge of the patient's breast, if possible. As shown in FIG. 4, the optical fiber 32 that receives the light signals following propagation through the patient's breast is then translated so as to move along a line that is also displaced from the suspicious region, albeit typically by a somewhat smaller distance. See also FIGS. 3a and 3b that designate the center of the suspicious region as CTR and that also depict the line 43 along which the optical fiber that receives the signals is moved. While the line along which the optical fiber that receives the light signals moves can be various lengths, the optical fiber that receives the light signals typically moves a distance of between about 40 millimeters and 60 millimeters with the center of the suspicious region approximately in the center of the range of motion.

The light signals that are delivered to the patient's breast during this further analysis are frequency-swept modulated. In this regard, the modulator 25, such as the network analyzer, modulates the amplitude of the light signal at a frequency that is swept through a predetermined range of frequency. For example, the amplitude of the light signal can be modulated at a frequency-swept from 0.3 MHz to 500 MHz. As such, at each different position of the optical fiber 32 that receives the signal that have propagated through the patient's breast, the amplitude of the light signal is frequency-swept modulated through the entire range of frequencies. As described above in conjunction with the creation of the shadow images, the patient's breast is preferably scanned by moving the detector along the line 43 twice, once while illuminating the patient's breast the light having a wavelength of 680 nanometers and another time while illuminating the patient's breast with light having a wavelength of 830 nanometers.

Figure 5A:
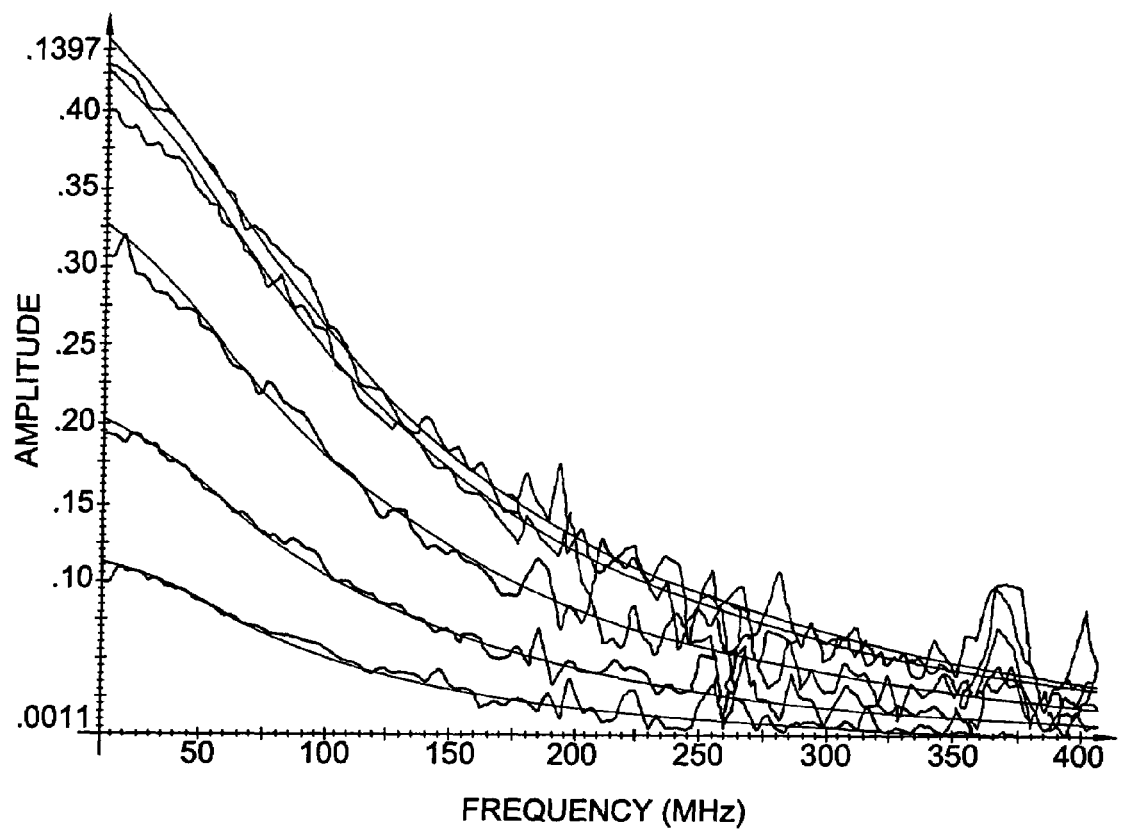
FIGS. 5a and 5b are exemplary graphs of the amplitude and phase of the light signals following propagation through a patient's breast wherein the amplitude of the light signals has been modulated over a predetermined range of frequencies.
Figure 5B:
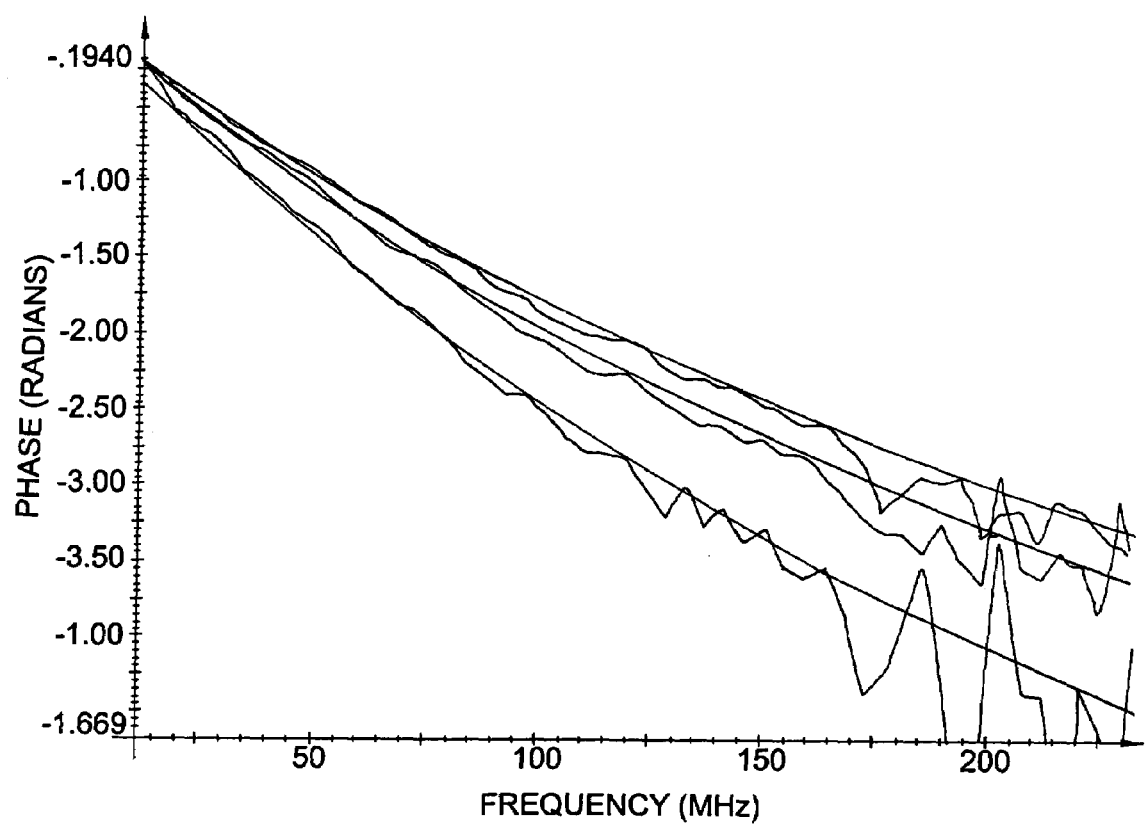

At each position of the optical fiber 32, the amplitude and phase of the light signals that have propagated through the patient's breast are detected over the range of modulation frequencies. In this regard, the amplitude and phase of the light signals detected at five different positions for light having a wavelength of 680 nanometers over the entire range of modulation frequencies are depicted in FIGS. 5a and 5b by differently colored curves. As will be apparent, however, the amplitude and phase of the light signals can be detected at any number of positions, such as twenty to thirty positions, without departing from the spirit and scope of the present invention. By utilizing a conventional mathematical software program, such as MATLAB Version 5 that is commercially available from the Math Works, Inc. of Natick, Mass., the central controller or computer 40 can fit smooth curves, typically by a least squares technique, to the plot corresponding to each position of the optical fiber that receives the light signals following propagation through the patient's breast.

As known to those skilled in the art, the propagation of the light signals through the host medium, such as through the patient's breast, can be modeled as a diffusion equation which is dependent upon the absorption and scattering coefficients of the medium through which the light signals propagate, the modulation frequency, the position of the optical fiber 32 that detects the light signals following propagation through the patient's breast relative to the position of the optical fiber 28 that provides the light signals and the wavelength of the light signals. As will therefore be apparent to those skilled in the art, for each wavelength of light, the diffusion equation can be solved for the absorption and scattering coefficients based upon the system of smoothly fit curves representing the amplitude and phase of the light signals at different modulation frequencies and the various positions of the optical fiber that receives the signals following propagation through the patient's breast relative to the optical fiber 28 that delivers the light signals. Since the majority of the light photons upon which the foregoing solution of the diffusion equation is based have not passed through the suspicious region due to the displacement from the center CTR of the suspicious region SR from both the optical fiber that delivers the light signals and the line 43 along which the optical fiber that receives the light signals moves, the solution of the diffusion equation will provide a reference absorption coefficient and a reference scattering coefficient at each wavelength for the healthy breast tissue outside of the suspicious region. Thus, reference scattering coefficients for light signals have wavelengths of 680 nanometers and 830 nanometers, $\mu_s'^r{}_{680}$ and $\mu_s'^r{}_{830}$, and reference absorption coefficients for light signals having wavelengths of 680 nanometers and 830 nanometers, $\mu_{a680}{}^r$ and $\mu_{a830}{}^r$, can be determined.

Figure 6:
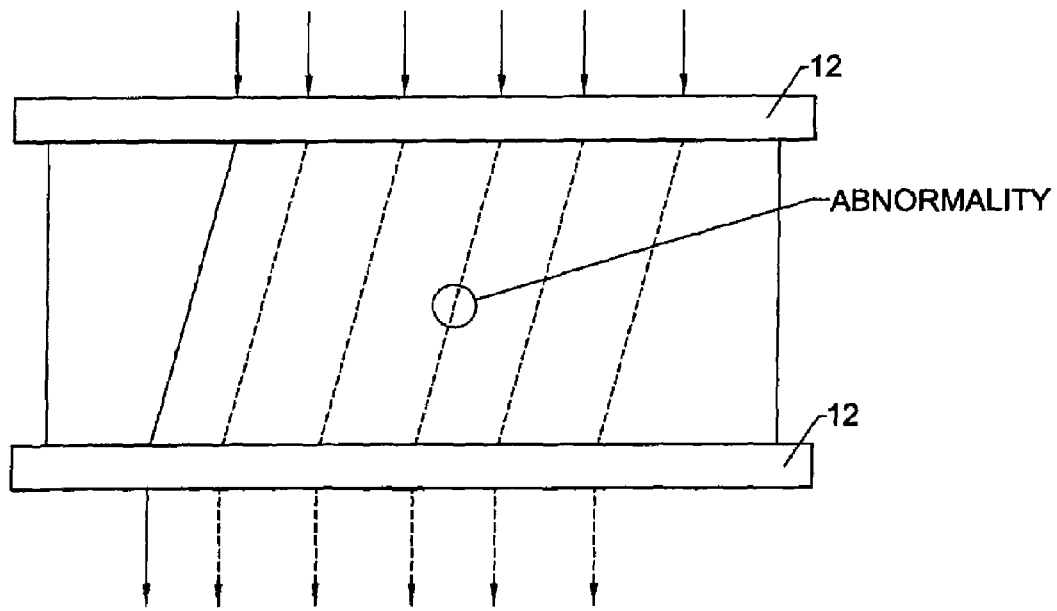
FIG. 6 is a schematic side elevational view of the more focused illumination of a suspicious region in which the optical fibers that deliver and receive the light signals are both moved in tandem, albeit in an offset relation.

The absorption coefficient $\tilde{\mu}_a{}^t$, within the suspicious region is then determined, wherein t designates a suspicious region, such as a tumor. In one embodiment, at least that portion of the patient's breast that includes the suspicious region SR is again scanned, albeit obliquely this time, in order to obtain the absorption coefficient $\tilde{\mu}_a{}^t$, within the suspicious region. In this regard, both the optical fiber 28 that delivers light signals to the patient's breast and the optical fiber 32 that receives the light signals following propagation through the patient's breast are moved along parallel lines 44 that extend through the center CTR of the suspicious region. However, the optical fiber that delivers the light signals to the patient's breast and the optical fiber that receives the light signals following propagation through the patient's breast are offset, typically by about 10 to 20 millimeters. See FIG. 6. Thus, even though the optical fibers that transmit the light signals and receive the light signals following propagation through the patient's breast move in tandem, the offset between the optical fibers remains the same at each position. As described above, the light signals are frequency-swept modulated through a predetermined range of frequencies, such as 0.3 MHz to 500 MHz, at each position.

Alternatively, the absorption coefficient $\tilde{\mu}_a{}^t$ may be determined based upon the results of further scanning of the suspicious region SR in the same manner described above in conjunction with the determination of the reference scattering and absorption coefficients. In this regard, the optical fiber 28 that provides the light signals can be fixed in a position displaced from the center CTR of the suspicious region and the optical fiber 32 that receives the light signals following propagation through the host medium can then be moved along a line 44 that is aligned with center of the suspicious region. Regardless of the scanning technique utilized to examine the suspicious region SR, the amplitude and phase of the light signals following propagation through the breast tissue are detected and plotted at each position across the entire range of frequencies. Thereafter, the central controller or computer 40 and, more particularly, conventional mathematical software program, such as MATLAB software, operating on the central computer, fits a smooth curve through the plot of the amplitude and phase of the light signals detected at each position. As described above, the diffusion equation is dependent upon the absorption and scattering coefficients of the breast tissue (including any tumor), the modulation frequency, the relative positions of the optical fibers 28, 32 that transmit the light signals and that receive the light signals following propagation through the patient's breast, the location of the suspicious region SR (typically the center CTR of the suspicious region) and the size d of the suspicious region. As will be apparent from the foregoing discussion, the scattering and absorption coefficients and the size of the suspicious region are unknown, although the remainder of the parameters are known. In order to solve this diffusion equation for the unknown parameters at each wavelength, the scattering coefficient is set equal to the reference scattering coefficient previously determined since it is not believed that the scattering coefficient is altered significantly by a tumor or other abnormality. At each wavelength, the diffusion equation is then solved for the absorption coefficient, typically an average absorption coefficient, for that portion of the patient's breast that includes the suspicious region and the size of the suspicious region. As described above, the patient's breast is scanned with each of at least two different wavelengths, such as 680 nanometers and 830 nanometers. As such, the absorption coefficient of the suspicious region of the patient's breast at both 680 nanometers and 830 nanometers can be determined, i.e., $\tilde{\mu}_{a680}{}^t$ and $\tilde{\mu}_{a830}{}^t$ wherein t designates a suspicious region, such as a tumor.

A physiological parameter denominated the P-criteria can then be determined. In this regard, the P-criteria is defined as:

$$P = \frac{\tilde{\mu}_{a680}^t - \mu_{a680}^r}{\tilde{\mu}_{a830}^t - \mu_{a830}^r} = \frac{\Delta \mu_{a680}}{\Delta \mu_{a830}}$$

wherein $\Delta\mu_{a680}$ is the variation in the absorption coefficient for light having a wavelength of 680 nanometers between the suspicious region and the host medium, i.e., between a tumor and healthy breast tissue, and $\Delta\mu_{a830}$ is the variation in the absorption coefficient for light having a wavelength of 830 nanometers between the suspicious region and the host medium.

Based upon the relative absorption coefficients for light signals having wavelengths of 680 nanometers and 830 nanometers that was described above, the absolute value of the P-criteria is relatively low for healthy breast tissue and benign lesions and increases for suspicious regions that include malignant tumors in a relatively early stage. Although not wishing to be bound by theory, in necrosis in which at least the center of the tumor consists of dead tissue, the absolute value of the P-criteria may actually be significantly less than the absolute value of the P-criteria for healthy breast tissue and benign lesions. As such, the P-criteria is a physiological parameter that can be utilized to characterize the abnormality, such as being either a benign or malignant tumor and, if malignant, the relative stage of the tumor, without a biopsy or other invasive procedure.

In addition to the P-criteria, an $S_{var}$-criteria based upon the ratio of variations in the percent concentration of oxygenated hemoglobin between the suspicious region and the host medium to variations in the total hemoglobin concentration between the suspicious region and the host medium also serves as another physiological parameter. In this regard, the variations in the concentration of oxygenated hemoglobin $\Delta[HbO_2]$, the concentration of deoxygenated hemoglobin $\Delta[Hb]$ and the total hemoglobin concentration $\Delta[Hb]_{total}$ are defined as follows:

$$\Delta[HbO_2] = [HbO_2]^t - [HbO_2]^r$$
$$\Delta[Hb] = [Hb]^t - [Hb]^r$$
$$[Hb]_{total}^t = [HbO_2]^t + [Hb]^t$$
$$[Hb]_{total}^r = [HbO_2]^r + [Hb]^r$$
$$\Delta[Hb]_{total} = [Hb]_{total}^t - [Hb]_{total}^r$$

wherein $[HbO_2]$ is the concentration of oxygenated hemoglobin, $[Hb]$ is the concentration of deoxygenated hemoglobin, $[Hb]$total is the total hemoglobin concentration and the superscripts t and r designate the suspicious region (or tumor) and the reference (or host) medium, respectively.

By way of background, an S-criteria is commonly utilized to define the percent concentration of oxygenated hemoglobin as defined below:

$$S = \frac{[HbO_2]}{[HbO_2] + [Hb]}$$

For a specific wavelength $\lambda$ of light the concentration of oxygenated hemoglobin and the concentration of deoxygenated hemoglobin can be related to the absorption coefficient through respective extinction coefficients as follows:

$$\mu_a^\lambda = \in_{HbO_2}^\lambda [HbO_2] + \in_{Hb}^\lambda [Hb]$$

wherein $\in_0 HbO^\lambda$ and $\in_{Hb}^\lambda$ are the extinction coefficients for light having a wavelength $\lambda$ for oxygenated hemoglobin and deoxygenated hemoglobin, respectively. These extinction coefficients are well known for different wavelengths of light. For example, the extinction coefficient for oxygenated hemoglobin is 974 and 2332 for light having a wavelength of 680 nanometers and 830 nanometers, respectively, and the extinction coefficient for deoxygenated hemoglobin is 5871 and 1791 for light having a wavelength of 680 nanometers and 830 nanometers, respectively. By scanning the patient's breast with light having at least two different wavelengths, such as 680 nanometers and 830 nanometers, a pair of equations relating the absorption coefficients to the concentrations of oxygenated hemoglobin and deoxygenated hemoglobin can be solved for the concentration for oxygenated hemoglobin and deoxygenated hemoglobin as set forth below:

$$[HbO_2] = \frac{\tilde{\mu}_{a680}^t \epsilon_{Hb}^{830} - \tilde{\mu}_{a830}^t \epsilon_{Hb}^{680}}{\epsilon_{HbO_2}^{680} \epsilon_{Hb}^{830} - \epsilon_{HbO_2}^{830} \epsilon_{Hb}^{680}};$$

$$[Hb] = \frac{\tilde{\mu}_{a830}^t \epsilon_{HbO}^{680} - \tilde{\mu}_{a680}^t \epsilon_{Hb}^{830}}{\epsilon_{HbO_2}^{680} \epsilon_{Hb}^{830} - \epsilon_{HbO_2}^{830} \epsilon_{Hb}^{680}}$$

Based upon the resulting values of $[HbO_2]$ and $[Hb]$, the S-criteria can be readily determined. In fact, by substituting the numerical values for the extinction coefficients and by defining k to equal $\mu_{a680}/\mu_{a830}$, the S-criteria can be redefined as:

$$S = \frac{5871 - k \cdot 1791}{k \cdot 541 + 4897}$$

Unfortunately, the S-criteria is not always a useful physiological parameter. However, the $S_{var}$-criteria should provide valuable diagnostic information and is therefore a useful physiological parameter. As described above, the $S_{var}$-criteria is based upon the ratio of variations in the percent concentration of oxygenated hemoglobin between the suspicious region and the host medium to variations in the total hemoglobin concentration between the suspicious region and the host medium. In order to understand the correlation between the S-criteria, the $S_{var}$-criteria and the P-criteria, consider that the absorption coefficients for a tumor and for a host or reference medium to light having a wavelength of 680 nanometers can be defined as follows:

$$\tilde{\mu}_{a680}^t = \epsilon_{HbO_2}^{680} [HbO_2]^t + \epsilon_{Hb}^{680} [Hb]^t$$

$$\mu_{a680}^r = \epsilon_{HbO_2}^{680} [HbO_2]^r + \epsilon_{Hb}^{680} [Hb]^r$$

As such, the variation in the absorption coefficient between the suspicious region and the host medium to light having a wavelength of 680 nanometers can be defined as:

$$\Delta\mu_{a680} = \tilde{\mu}_{a680}^t - \mu_{a680}^r = \epsilon_{HbO_2}^{680} \Delta[HbO_2] + \epsilon_{Hb}^{680} \Delta[Hb]$$

Likewise, the variation in the absorption coefficient between the suspicious region and the host medium to light having a wavelength of 830 nanometers can be defined as:

$$\Delta\mu_{a830} = \tilde{\mu}_{a830}^t - \mu_{a830}^r = \epsilon_{HbO_2}^{830} \Delta[HbO_2] + \epsilon_{Hb}^{830} \Delta[Hb]$$

As described above, the P-criteria can also be defined as:

$$P = \frac{\Delta\mu_{a680}}{\Delta\mu_{a830}}$$

Based upon the foregoing mathematical definitions and by substituting the numerical values of the extinction coefficients, the $S_{var}$-criteria can be rewritten as:

$$S_{var} = \frac{\Delta[HbO_2]}{\Delta[Hb]_{total}} = \frac{5871 - P \cdot 1791}{P \cdot 541 + 4897}$$

As will be apparent, the $S_{var}$-criteria therefore has the same form as the S-criteria and has the same dependence upon the P-criteria as the S-criteria does upon k. As such, once the P-criteria has been determined as described above, the $S_{var}$-criteria can be readily determined by the central controller or computer 40, or vice versa. Although not wishing to be bound by theory, it is believed that smaller values of the $S_{var}$-criteria will generally indicate a malignancy, while larger values of the $S_{var}$-criteria will indicate other types of abnormalities, such as a benign lesion.

Another physiological parameter of interest that is mathematically related to the P-criteria and that can be determined by the central controller or computer 40 is the Q-criteria. The Q-criteria is the ratio of the relative differences of the absorption coefficients of the suspicious region and the host or reference medium to light having two different wavelengths, i.e., 680 nanometers and 830 nanometers, and is defined as follows:

$$Q = \frac{(\tilde{\mu}_{a680}^t / \mu_{a680}^r) - 1}{(\tilde{\mu}_{a830}^t / \mu_{a830}^r) - 1}$$

As such, the Q-criteria is also related to the P-criteria as follows:

$$Q = \frac{\mu_{a830}^r}{\mu_{a680}^r} \cdot P$$

The Q-criteria is therefore directly related to the P-criteria and can be utilized to characterize abnormalities in much the same fashion as the P-criteria. In this regard, the absolute value of the Q-criteria is relatively low for healthy breast tissue and increases for suspicious regions that include malignant tumors in a relatively early stage. Although not wishing to be bound by theory, in necrosis in which at least the center of the tumor consists of dead tissue, the absolute value of the Q-criteria may also actually be significantly less than the absolute value of the Q-criteria for healthy breast tissue. As such, the Q-criteria is another physiological parameter that can be utilized to characterize the abnormality, such as being either a benign or malignant tumor and, if malignant, the relative stage of the tumor, without a biopsy or other invasive procedure.

Based upon the physiological parameters determined by the detection method and apparatus of the present invention, i.e., the P-criteria, the $S_{var}$-criteria and the Q-criteria, the abnormality can be characterized, such as a malignant or benign tumor, without a biopsy or other invasive procedure.

In order to buttress the characterization of the abnormality based upon the physiological parameters, the shadow image permits a visual determination to be made as well. In this regard, it is believed that malignant tumors include not only the tumor itself, but also a blood cloud of tissue surrounding the tumor. While the blood cloud is not generally depicted by x-rays, the blood cloud surrounding the tumor does attenuate the light signals to a greater degree than healthy breast tissue. As such, a shadow image constructed from light signals having either of the wavelengths or from the ratio of the shadow images can be compared to an x-ray image of the patient's breast. If the suspicious region SR in which the light signals have been significantly attenuated as depicted by the shadow image is substantially larger than the tumor or other abnormality as depicted by the x-ray image, the abnormality may be consistent with the image of a malignant tumor. Alternatively, if the suspicious region depicted in the shadow image is approximately the same size as the abnormality depicted in the x-ray, a benign tumor or other non-malignant abnormality would likely be present. In order to assist in the comparison of the relative sizes of the suspicious region of the shadow image and the x-ray image, the shadow image can be overlaid upon the x-ray image in order to compare the relative sizes. For example, the x-ray image may be scanned into the central controller or computer 40 and sized to match the shadow image to facilitate the overlaying of the images and the visual comparison. As such, a visual comparison of the suspicious region depicted in a shadow image to an x-ray image can serve to buttress the characterization of the abnormality that is otherwise based upon the P-criteria, the $S_{var}$-criteria and the Q-criteria.

Based upon the results of the oblique scanning of at least the suspicious region SR during which the optical fibers 28, 32 that transmit and receive the light signals are offset, the relative positions of the optical fibers at which the largest percentage of the light signals propagated through the abnormality can be determined, thereby defining a line extending between the optical fibers along which the abnormality lies. Likewise, the results of the initial scanning of the patient's breast during the creation of the shadow images can be reviewed and the relative positions of the optical fibers at which the largest percentage of the light signals propagated through the abnormality can also be determined, thereby defining another line extending between the optical fibers along which the abnormality lies. Since an abnormality generally attenuates the light signals to a much greater degree than the surrounding host medium, the relative positions of the optical fibers at which the largest percentage of the light signals propagated through the abnormality generally correspond to the relative positions of the optical fibers at which the amplitude of the light signals detected following propagation through the host medium has been most greatly attenuated. Utilizing stereotactic principles, the position, including the depth, of the abnormality can therefore be determined as the intersection of the two lines along with the abnormality lies.

While the position of the abnormality is preferably determined following the oblique scanning of the suspicious region SR as described above, the detection method and apparatus can be configured such that shadow images are obtained with the optical fibers in different orientations in order to permit the position, including the depth, of the abnormality to be determined directly from the shadow images. In this embodiment, the pair of plates 12 are typically designed to be rotated relative to the patient, such as by about 90°, in order to obtain a shadow image from a different orientation.

In order to further protect the photomultiplier tube 34 and to further guard against deleterious edge effects, the patient's breast can also be illuminated with a continuous wave (cw) light source, such as a fiber optic pigtaildiode laser 50 that emits a continuous wave signal having a wavelength of between about 950 nanometers and 980 nanometers and, most preferably, about 980 nanometers. In this regard, a laser diode that emits a continuous wave signal having a wavelength of 980 nanometers is particularly advantageous since light having a wavelength of 980 nanometers is dramatically attenuated by a malignant lesion as compared to benign tissue and is therefore quite apparent from a review of the continuous wave signals following propagation through the patient's breast.

In this regard, the continuous wave signal is supplied concurrent with a light signal of either 680 nanometers or 830 nanometers. Additionally, the continuous wave light signal having a wavelength of 980 nanometers is also detected following propagation through the patient's breast concurrent with light having a wavelength of either 680 nanometers or 830 nanometers. As shown in FIG. 2, however, the continuous wave light signal having a wavelength of 980 nanometers is split from the light signal having a wavelength of either 680 nanometers or 830 nanometers by a splitter 51 and is directed to an avalanche photodiode 52, the output of which is directed to a multimeter 54. The multimeter, in turn, provides a signal to the central controller or computer 40 that is representative of the power level of the continuous wave light signal. If the central controller or computer determines that the continuous wave light signals having a wavelength of 980 nanometers have an intensity that exceed a predetermined threshold, the central controller or computer can close a shutter 56 that is disposed upstream of the photomultiplier tube 34 in order to prevent damage to the photomultiplier tube. Instances in which such high intensity signals arise may occur, for example, during attempts to scan regions outside of the patient's breast that are not covered by the opaque material. If not blocked by the shutter, the photomultiplier tube might otherwise be damaged or at least be caused to generate an erroneous output if exposed to the excessively intense signals.

In addition to providing a measure of protection for the photomultiplier tube 34, the continuous wave signal having a wavelength of 980 nanometers can also generate an image, much like the shadow image described above and depicted in FIGS. 3a and 3b. In this regard, the continuous wave signals having a wavelength of 980 nanometers can be detected following propagation through the patient's breast and an image of the amplitude of the detected signal at each of a plurality of positions can be constructed. Since light signals having a wavelength of 980 nanometers are particularly sensitive to the increased absorption of malignant tumors, the resulting image can further buttress the characterization of the abnormality as a malignant tumor if those regions representing substantially attenuated light signals at 980 nanometers correspond to suspicious regions SR identified within the shadow images.

Accordingly, the method and apparatus of the present invention permits abnormalities to be detected within a host medium in a more reliable and cost effective manner than conventional techniques. In addition, the method and apparatus of the present invention permits physiological parameters, such as the P, $S_{var}$ and Q criteria, that at least partially define the abnormality to be determined in order to characterize the abnormality. As such, the method and apparatus of the present invention can be advantageously utilized to provide early detection of suspicious lesions, such as tumors, within a patient's breast and to appropriately characterize the suspicious lesions, such as being either malignant or benign, based upon physiological parameters that are determined from the detected signals without requiring a biopsy or other invasive procedure. By facilitating early detection and characterization of suspicious lesions within the patient's breast, the patient's chances of survival are substantially increased.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for detecting an abnormality in a host medium comprising:
    illuminating the host medium at a plurality of different positions with frequency-swept modulated signals;
    detecting signals following propagation through the host medium and the abnormality within the host medium;
    creating a shadow image based upon the detected signals in which the abnormality is depicted as a suspicious region;
    illuminating at least that portion of the host medium that contains the suspicious region with frequency-swept modulated signals, following creation of the shadow image, wherein the signals are frequency-swept modulated across a larger range of frequencies during the illumination of the suspicious region than during the initial illumination of the host medium;
    detecting the frequency-swept modulated signals following propagation through at least that portion of the host medium that contains the suspicious region; and
    characterizing the abnormality based upon the detected frequency-swept modulated signals.

2. A method according to claim 1 wherein said initial illumination step comprises illuminating the host medium with signals having at least two different wavelengths.

3. A method according to claim 2 wherein said initial detecting step comprises detecting at least an amplitude of the signals following propagation through the host medium and the abnormality within the host medium.

4. A method according to claim 3 further comprising forming a ratio of the amplitude of the signals detected during said initial detecting step at each of the different wavelengths.

5. A method according to claim 1 wherein said step of illuminating at least that portion of the host medium that contains the suspicious region comprises illuminating at least that portion of the host medium that contains the suspicious region with signals having at least two different wavelengths.

6. A method according to claim 5 further comprising a step of determining a P-criteria for at least one of a plurality of positions within at least that portion of the host medium that contains the suspicious region following said second detecting step, wherein the P-criteria is at least partially based upon coefficients of absorptivity for signals having the different wavelengths at the respective position.

7. A method according to claim 1 further comprising a step of determining an $S_{var}$-criteria for at least one of a plurality of positions within at least that portion of the host medium that contains the suspicious region following said second detecting step, wherein the $S_{var}$-criteria is at least partially based upon a variation in percent concentration of oxygenated hemoglobin between the abnormality and the host medium and a variation in total hemoglobin concentration between the abnormality and the host medium at the respective position.

8. A method according to claim 1 further comprising:
    illuminating a portion of the host medium at a plurality of different positions displaced from the suspicious region with signals having at least two different wavelengths;
    detecting the signals following propagation through the host medium; and
    determining a reference scattering coefficient and a reference absorption coefficient for the host medium based upon the detected signals.

9. A method according to claim 8 further comprising determining an absorption coefficient and a size of the abnormality based on setting a scattering coefficient of the abnormality equal to the reference scattering coefficient and further based upon the frequency-swept modulated signals that are detected following propagation through at least that portion of the host medium that contains the suspicious region.

10. A method according to claim 9 further comprising determining a location of the abnormality within the host medium following said second detecting step.

11. A method according to claim 1 wherein the host medium is a breast, and wherein the method further comprises compressing the breast between a pair of plates prior to said initial illumination step.

12. A method according to claim 1 wherein the host medium is a breast, and wherein the method further comprises applying oil to the breast prior to said initial illumination step.

13. A method for detecting an abnormality in a host medium comprising:
    illuminating the host medium at a plurality of different positions that cover a broad portion of the host medium to facilitate generation of a shadow image;
    detecting signals following propagation through the host medium and the abnormality within the host medium;
    creating the shadow image based upon the detected signals in which the abnormality is depicted as a suspicious region;
    illuminating that portion of the host medium that contains the suspicious region with frequency-swept modulated signals, following creation of the shadow image, wherein illuminating the suspicious region comprises positioning a light source that is capable of emitting light that propagates in a first direction proximate the suspicious reason but at a position offset from at least one of the suspicious region and a detector in a direction transverse to the first direction;
    detecting the frequency-swept modulated signals with the detector following propagation through at least that portion of the host medium that contains the suspicious region; and
    characterizing the abnormality based upon the detected frequency-swept modulated signals.

14. A method according to claim 13 wherein said second detecting step comprises one of moving a detector through a plurality of positions including at least one position aligned with the suspicious region and moving a detector along a linear path displaced from the suspicious region.

15. A method for detecting an abnormality in a host medium comprising:
- illuminating the host medium at a plurality of different positions;
- detecting signals following propagation through the host medium and the abnormality within the host medium;
- creating a shadow image based upon the detected signals in which the abnormality is depicted as a suspicious region;
- illuminating at least that portion of the host medium that contains the suspicious region with frequency-swept modulated signals, following creation of the shadow image;
- detecting the frequency-swept modulated signals following propagation through at least that portion of the host medium that contains the suspicious region; and
- characterizing the abnormality based upon the detected frequency-swept modulated signals,
- wherein said second illuminating and detecting steps comprise:
- positioning a light source and a detector on opposite sides of the host medium in an offset relation and out of alignment with one another; and
- moving the light source and the detector in tandem such that the offset relation is maintained.

16. An apparatus for detecting an abnormality in a host medium comprising:
- a light source for generating signals that propagate in a first direction and illuminate the host medium at a plurality of different positions;
- a modulator for applying frequency-swept modulation to the signals generated by said light source prior to illuminating the host medium;
- a detector for detecting signals following propagation through the host medium and the abnormality within the host medium;
- a display for presenting a shadow image based upon the detected signals in which the abnormality is depicted as a suspicious region; and
- a positioner for positioning said light source relative to the host medium such that said light source illuminates the host medium at the plurality of different positions, wherein said positioner initially positions said light source at a plurality of different positions that cover a broad portion of the host medium to facilitate generation of the shadow image, and wherein said positioner subsequently positions said light source proximate that portion of the host medium that includes the suspicious region, following generation of the shadow image, to facilitate characterization of the abnormality,
- wherein said positioner also positions said detector relative to the host medium, and wherein said positioner is capable of positioning said light source proximate the suspicious region but in an offset relation in a direction transverse to the first direction from one of said detector and the suspicious region.

17. An apparatus according to claim 16 wherein said positioner maintains said light source and said detector in alignment while initially positioning said light source and said detector at a plurality of different positions that cover a broad portion of the host medium to facilitate generation of the shadow image.

18. An apparatus according to claim 16 wherein said positioner comprises at least two X-Y linear motorized stages.

19. An apparatus according to claim 16 wherein said modulator comprises a frequency-swept network analyzer.

20. An apparatus according to claim 16 wherein the host medium is a breast, and wherein the apparatus further comprises a pair of plates separated by a distance sufficient to receive the breast of a patient.

21. An apparatus according to claim 20 further comprising an adjustable belt extending between said plates proximate the breast, said adjustable belt capable of being tightened about the breast such that the breast fills a region defined by said pair of plates and said adjustable belt, thereby facilitating imaging of the breast.

22. An apparatus according to claim 20 further comprising an opaque material that fills a region defined by said plates that is unfilled by the breast.

23. An apparatus according to claim 22 further comprising a background light source for illuminating any regions of separation between said opaque material and the breast.

24. An apparatus according to claim 20 further comprising a separation detector for measuring the distance by which said pair of plates are separated.

25. An apparatus according to claim 16 wherein said detector is a photomultiplier tube.

26. An apparatus according to claim 16 further comprising a diaphragm for selectively controlling an intensity of light that is presented to said detector.

27. An apparatus according to claim 16 wherein said light source comprises a first fiber optic pigtail infrared diode laser capable of emitting signals having a power level of between 100 milliwatts and 500 milliwatts and a wavelength of between 810 nanometers and 840 nanometers.

28. An apparatus according to claim 27 wherein said light source comprises a second fiber optic pigtail infrared diode laser capable of emitting signals having a power level of between 100 milliwatts and 500 milliwatts and a wavelength of between 670 nanometers and 700 nanometers.

29. An apparatus according to claim 16 further comprising:
- a reference light source for also illuminating the host medium with reference signals;
- a reference detector for detecting the reference signals following propagation through the host medium and the abnormality within the host medium; and
- a shutter for preventing further detection by said detector if said reference detector detects that an amplitude of the reference signals exceeds a predetermined threshold.

30. An apparatus according to claim 29 wherein said reference light source comprises a fiber optic pigtail diode laser operating in a continuous wave mode and capable of emitting signals having a wavelength of between 950 nanometers and 980 nanometers.

* * * * *